(12) United States Patent
Haiat et al.

(10) Patent No.: US 11,490,943 B2
(45) Date of Patent: Nov. 8, 2022

(54) DEVICE FOR INSERTING A SURGICAL IMPLANT

(71) Applicants: Centre National de la Recherche Scientifique, Paris (FR); Université Paris XII Val de Marne, Creteil (FR)

(72) Inventors: Guillaume Haiat, Rungis (FR); Giuseppe Rosi, Paris (FR); Antoine Tijou, Créteil (FR)

(73) Assignees: CENTRE NATIONAL DE LA RECHERCHE SCIENTIFIQUE, Paris (FR); Université Paris XII Val de Marne, Creteil (FR)

( * ) Notice: Subject to any disclaimer, the term of this patent is extended or adjusted under 35 U.S.C. 154(b) by 316 days.

(21) Appl. No.: 16/651,697

(22) PCT Filed: Sep. 27, 2018

(86) PCT No.: PCT/EP2018/076228
§ 371 (c)(1),
(2) Date: Mar. 27, 2020

(87) PCT Pub. No.: WO2019/063675
PCT Pub. Date: Apr. 4, 2019

(65) Prior Publication Data
US 2020/0229858 A1 Jul. 23, 2020

(30) Foreign Application Priority Data
Sep. 29, 2017 (FR) ........................ 1759130

(51) Int. Cl.
*A61B 17/92* (2006.01)
*A61F 2/46* (2006.01)
(Continued)

(52) U.S. Cl.
CPC .......... *A61B 17/921* (2013.01); *A61F 2/4607* (2013.01); *A61B 17/72* (2013.01);
(Continued)

(58) Field of Classification Search
CPC . A61B 17/92; A61B 17/921; A61B 2017/922; A61B 2017/924;
(Continued)

(56) References Cited

U.S. PATENT DOCUMENTS 9,931,151 B2 * 4/2018 Donald ................ A61B 90/30
10,426,541 B2 * 10/2019 Haiat ..................... A61B 17/92
(Continued)

FOREIGN PATENT DOCUMENTS

| EP | 2923677 A1 | 9/2015 |
|----|------------|--------|
| FR | 3019031 A1 | 10/2015 |
| IN | 2013-03261 A | 4/2016 |

OTHER PUBLICATIONS

International Search Report issued in Application No. PCT/EP2018/076228, dated Jan. 25, 2019 (7 pages).
(Continued)

*Primary Examiner* — Eric S Gibson
(74) *Attorney, Agent, or Firm* — Osha Bergman Watanabe & Burton LLP

(57) ABSTRACT

A device for forcefully inserting a surgical implant in a recipient bone by impaction, comprising an impactor (10) that exerts an impaction force on the implant and is associated with at least one sensor (12). The sensor (12) measures a value from among the exerted impaction force and the deformation of the impactor (10) and provides a measurement signal representing the temporal variation of said value during an impact. The sensor (12) is connected to a processing unit (30) that is configured to compute, on the basis of the temporal variation of said value during the
(Continued)

impact, an indicator representing the level of contact between the implant and the recipient bone. The indicator corresponds to the duration separating the instant corresponding to the first maximum amplitude peak of the measurement signal from the instant corresponding to the second maximum amplitude peak of the measurement signal. The implant can be a femoral rod (2).

15 Claims, 3 Drawing Sheets

(51) Int. Cl.
A61B 90/00 (2016.01)
A61B 17/72 (2006.01)
A61B 17/00 (2006.01)

(52) U.S. Cl.
CPC ............... A61B 2017/0011 (2013.01); A61B 2017/00022 (2013.01); A61B 2017/00119 (2013.01); A61B 2017/924 (2013.01); A61B 2090/065 (2016.02); A61F 2002/4681 (2013.01)

(58) Field of Classification Search
CPC ........ A61B 2017/925; A61B 2017/927; A61B 2017/928; A61F 2/4607
See application file for complete search history.

(56) References Cited

U.S. PATENT DOCUMENTS

| | | | | |
|---|---|---|---|---|
| 10,912,655 B2* | 2/2021 | Behzadi | ................... | A61F 2/34 |
| 11,026,809 B2* | 6/2021 | Behzadi | ................. | A61F 2/4637 |
| 11,234,840 B2* | 2/2022 | Behzadi | ................. | A61F 2/4609 |
| 2015/0196343 A1* | 7/2015 | Donald | ................. | A61B 17/92 |
| | | | | 606/100 |
| 2015/0282856 A1* | 10/2015 | Haiat | ................. | A61F 2/4609 |
| | | | | 606/100 |
| 2017/0196708 A1* | 7/2017 | Behzadi | ............. | A61B 17/1666 |
| 2017/0196711 A1* | 7/2017 | Behzadi | ............. | A61B 17/1659 |
| 2017/0340456 A1* | 11/2017 | Behzadi | ................. | A61B 7/023 |
| 2018/0116821 A1* | 5/2018 | Johannaber | ................. | A61F 2/46 |
| 2019/0350724 A1* | 11/2019 | Behzadi | ................. | A61B 90/13 |
| 2019/0350726 A1* | 11/2019 | Behzadi | ................. | A61F 2/4657 |
| 2020/0138598 A1* | 5/2020 | Behzadi | ................. | A61F 2/4637 |
| 2020/0229858 A1* | 7/2020 | Haiat | ................. | A61F 2/4657 |
| 2020/0246053 A1* | 8/2020 | Haiat | ................. | A61B 17/921 |
| 2020/0294423 A1* | 9/2020 | Blain | ................. | A61B 34/20 |
| 2021/0145603 A1* | 5/2021 | Dun | ................. | A61F 2/4609 |
| 2021/0161576 A1* | 6/2021 | Haiat | ................. | A61B 17/92 |
| 2021/0244487 A1* | 8/2021 | Beck | ................. | A61F 2/4607 |
| 2021/0361336 A1* | 11/2021 | Adekanmbi | .......... | A61F 2/4657 |

OTHER PUBLICATIONS

Written Opinion issued in Application No. PCT/EP2018/076228, dated Jan. 25, 2019 (6 pages).

Office Action issued in Indian Application No. 202047013663 dated Mar. 7, 2022 (6 pages).

* cited by examiner

DEVICE FOR INSERTING A SURGICAL IMPLANT

TECHNICAL FIELD

The invention relates to a device for inserting a surgical implant into a receiving bone, by impaction. This device comprises a percussion tool, or impactor, for exerting an impact force on the surgical implant in order to forcibly insert the implant into the receiving bone.

BACKGROUND

In the present disclosure, the concept of surgical implant is not limited to surgical implants per se, but also includes surgical instruments temporarily inserted into a receiving bone. This concept covers, in particular, all orthopedic prosthesis implants intended to replace a deficient joint, in particular implants for hip, knee, shoulder, spine, elbow, or ankle prostheses, and the fitting instruments used to prepare the receiving bone to receive the prosthesis.

The invention relates more particularly, but not exclusively, to the fitting of a hip prosthesis. The vast majority of hip prostheses have in common a first part fixed to the femur and a second part fixed to the pelvis. The first part comprises a femoral stem intended to be forcibly inserted into the medullary canal of the femur and a prosthetic head consisting of a spherical piece, mounted on the femoral stem and replacing the head of the femur. The second part comprises a prosthetic acetabulum intended to be inserted into the acetabular cavity located on the lateral face of the iliac bone of the pelvis, to replace the articular part of the pelvis. The prosthetic acetabulum may comprise an acetabular cup, which is an approximately hemispherical piece, generally made of metal, inserted into the acetabular cavity and in which is placed an insert with which the prosthetic head is articulated.

The insertion of the femoral stem into the medullary canal is generally accomplished by impaction using an impactor, typically a hammer. An ancillary tool may also be used, the practitioner using the impactor to strike the ancillary tool, which transmits the impaction force to the femoral stem.

As the number of impacts increases, the stem becomes embedded in the medullary canal. Because the stem becomes embedded over a large part of its length, the relative movement between the stem and the femur is considerable. The level of contact between the stem and the surrounding femur depends on this embedding. This level of contact is generally characterized by the BIC ratio, which stands for bone to implant contact ratio, which is the percentage of the surface area of the implant in contact with the bone. The further the stem is pushed in, the greater the surface area of the stem in contact with the femur.

The practitioner primarily wishes to monitor the embedding of the stem in the femur and determine the moment at which the level of contact between the stem and the femur is optimal or, at the very least, satisfactory. The success of the operation depends both on a sufficient level of contact between the stem and the femur and on avoiding damage, in particular avoiding inducing a fracture or microcracks in the femur during insertion. If the femoral stem is insufficiently inserted into the femur, this may result in micromovements of the stem, which may require another surgical intervention.

A compromise must therefore be found between a number of impacts high enough to obtain a satisfactory level of contact between the stem and the femur, and low enough not to risk damaging the femur. However, it is difficult for the practitioner to himself reliably assess the correct number of impacts. To be specific, it is difficult for him to know precisely when to stop striking the femoral stem with the impactor.

In this context, and more generally in the context of forcible insertion of a surgical implant into a receiving bone by impaction, one aim of the invention is to propose a device making it possible to provide, during the surgical operation, reliable information on the level of contact between the implant and the receiving bone, thus enabling the practitioner to ascertain, in real time, when he should stop striking the implant with the impactor.

Patent document FR 3019031 describes a technique for assisting the fitting of an orthopedic implant, which comprises calculating an indicator that is correlated to the force required to tear out the implant and that reflects the stability of the implant. This indicator is very useful in many applications, in particular for the fitting of a prosthetic acetabulum in the acetabular cavity. However, in applications such as the insertion of a femoral stem, other indicators may be more useful, or at least as useful to the practitioner. The use of several indicators could also prove to be advantageous in certain applications.

GENERAL PRESENTATION

The invention relates to a device for forcibly inserting a surgical implant into a receiving bone, by impaction. This device comprises an impactor for impacting an impact surface coupled to said surgical implant and exerting an impact force on the implant.

The impactor is associated with at least one sensor adapted for measuring a magnitude out of the impact force exerted and the deformation of the impactor, and of providing a measurement signal representing the temporal variation of said magnitude during an impact.

The sensor (i.e. said at least one sensor) is connected to a processing unit configured to determine, on the basis of the temporal variation of said magnitude during the impact, an indicator representative of the level of contact between the implant and the receiving bone. The electronic connection between the sensor and the processing unit may be wired or not.

The proposed solution is based on the implementation of one or more sensors associated with the impactor and delivering a measurement signal, the recording and analysis of this signal making it possible to determine an indicator indicating the level of contact between the implant and the receiving bone. When several sensors are used, the signals respectively delivered by these sensors may, for example, be averaged or combined to obtain the measurement signal which will be analyzed and on the basis of which the indicator will be calculated.

Such a device makes it possible, during the surgical implant insertion operation, to inform the practitioner in real time about the level of contact reached between the implant and the receiving bone. In addition to its reduced cost, this device has the advantage of being simple to use. In particular, with this device, the practitioner's gesture during the operation remains the same. Therefore, the practitioner does not have to learn new gestures and can benefit from the experience he has already acquired with conventional devices.

The proposed indicator corresponds to the duration of a time window, the start of this time window being defined with respect to an instant corresponding to the first peak of maximum amplitude of the measurement signal and the end of this time window being defined with respect to an instant corresponding to the second peak of maximum amplitude of the measurement signal. The indicator thus calculated has been shown to be correlated with the level of contact between the implant and the receiving bone and to constitute a reliable indicator.

In some embodiments, the device further comprises an alert system connected to the processing unit and interacting with the latter so as to emit an alert signal when the indicator becomes less than (i.e. falls below) a predetermined threshold value. This threshold value can be determined experimentally. For example, tests are carried out, the threshold value chosen being the value of the indicator from which there is a sufficient level of contact between the implant and the receiving bone. In particular, the threshold value can be between 0.1 and 1 ms.

Thus, the fact that the duration of said time window becomes less than a certain, predetermined, duration is used as a condition for emitting the alert signal (e.g. a light, a sound, a vibration, etc.). The practitioner, alerted by this signal, then knows that he must stop impacting the implant, the level of contact between the implant and the bone being considered to be optimal or, in any case, sufficient.

Of course, other conditions relating to the indicator itself or to the variation in the indicator during a series of successive impacts could be used to trigger an alert, without departing from the scope of the invention. In particular, it is possible to take advantage of the fact that, when a satisfactory level of bone-implant contact is reached, the proposed indicator tends to stabilize (i.e. converges to a stationary value).

In some embodiments, the processing unit detects, in the measurement signal, the first peak of maximum amplitude and the peak of maximum amplitude following the first peak, the latter peak being considered as the second peak of maximum amplitude only if the measurement signal between these two peaks becomes less than a predetermined limit value (i.e. if the measurement signal falls below the limit value before rising back above this value to form the second peak). In particular, the limit value may be between 1 and 20% of the maximum amplitude of the first peak. For example, the peak of maximum amplitude following the first peak is considered as the second peak of maximum amplitude only if the measurement signal drops below a limit value equal to 5% of the maximum amplitude of the first peak.

This precaution makes it possible to avoid measurement errors linked to a phenomenon of duplication of the first peak, which has been observed in a small number of cases. During such a phenomenon, the two peaks resulting from duplication of the first peak are close to one another and the inventors realized that the measurement signal did not have time to decrease significantly between these two peaks. Thus, the solution consisting in verifying that the measurement signal has sufficiently decreased before reaching the second peak of maximum amplitude makes it possible to avoid wrongly considering the duplicate of the first peak as the second peak of maximum amplitude, and therefore avoid a measurement error on the indicator. Of course, other methods of analysis of the measurement signal could be envisaged to detect a duplication of the first peak and to avoid measurement errors in such a case.

In some embodiments, the impactor has a striking face for impacting the impact surface and the sensor is a force sensor for measuring the impact force and providing a measurement signal representing the temporal variation of the impact force during an impact.

In other embodiments, the impactor has a striking face for impacting the impact surface, an opposite face, opposite to the striking face, and side faces extending between the striking face and the opposite face, and the sensor is a deformation sensor for measuring the deformation of the impactor and providing a measurement signal representing the temporal variation of the deformation of the impactor during an impact.

In some embodiments, the impactor is a hammer, or equivalent, and comprises a gripping shaft topped by a striking head. In particular, the impactor may have substantially the same shape and the same weight as impactors commonly used to date. Thus, experienced practitioners are immediately able to handle the impactor correctly.

It will be noted that the impact surface may be directly coupled to the implant, in the sense that it may be one of the surfaces of the implant, or may be indirectly coupled to the implant, in the sense that it may be a surface of an instrument, or ancillary tool, itself coming into contact with the implant. In the latter case, the impactor exerts the impact force on the implant via the ancillary tool. In other words, the impact force is exerted on the ancillary tool and transmitted by the latter to the implant.

In some embodiments, the device comprises an ancillary tool having a rear end forming said impact surface and a front end for interacting with the implant, the impactor exerting the impact force on the implant via the ancillary tool.

The front end of the ancillary tool may cooperate with the implant by simple contact. Alternatively, the front end of the ancillary tool may be mechanically attached to the orthopedic implant in a removable manner, for example by screwing. Attaching the ancillary tool to the implant generally provides a better measurement signal. The ancillary tool is removable such that it may easily be detached from the implant once the latter is in position.

The present disclosure also relates to an assembly comprising a device as described above and a surgical implant, in particular a femoral stem.

The invention also relates to a method for forcibly inserting a surgical implant into a receiving bone, by impaction, wherein:
  a device as described above is provided,
  an impact force is exerted on the implant with the impactor, by impacting an impact surface coupled to the implant, so as to insert the implant,
  the indicator is calculated during successive impacts, and
  impacting of the impact surface is stopped when the indicator becomes less than a predetermined threshold value.

The surgical implant may be, but is not necessarily, a femoral stem. In this case, the femoral stem is impacted with the impactor so as to forcibly insert the stem into the medullary canal of the femur of a patient.

The advantages of such a method stem from the advantages of the device used.

The aforementioned features and advantages, as well as others, will emerge on reading the following detailed description of exemplary embodiments of the proposed device. This detailed description refers to the attached drawings.

BRIEF DESCRIPTION OF THE DRAWINGS

The attached drawings are schematic and are not to scale; their primary purpose is to illustrate the principles of the invention.

FIG. 1 shows an example of a device 1 for gradually inserting a surgical implant into a receiving bone, by impaction. In this example, the implant is an implant for a prosthesis, in particular a femoral stem 2 for a hip prosthesis. This stem 2 is intended to be inserted gradually by impaction into the medullary canal 3 of the femur 4 of a patient. The medullary canal 3 is, usually, previously prepared by the practitioner to receive the stem 2. In all cases, the dimensions of the stem 2 are slightly greater than the dimensions of the medullary canal 3 and the stem 2 is forcibly inserted into this canal.

The femoral stem 2 comprises a prosthetic neck 7 intended to protrude from the femur 4, with an end 7a that receives a sphere (not shown), and a tapered body 8 extending from the neck 7 with a cross section that decreases in the direction away from the neck 7. The body 8 is intended to be fully embedded in the femur 4. In FIG. 1, the body 8 is shown partially embedded in the femur 4. The neck 7 also has, next to its end 7a, a bearing surface 7b for an ancillary tool 20.

Figure 1:
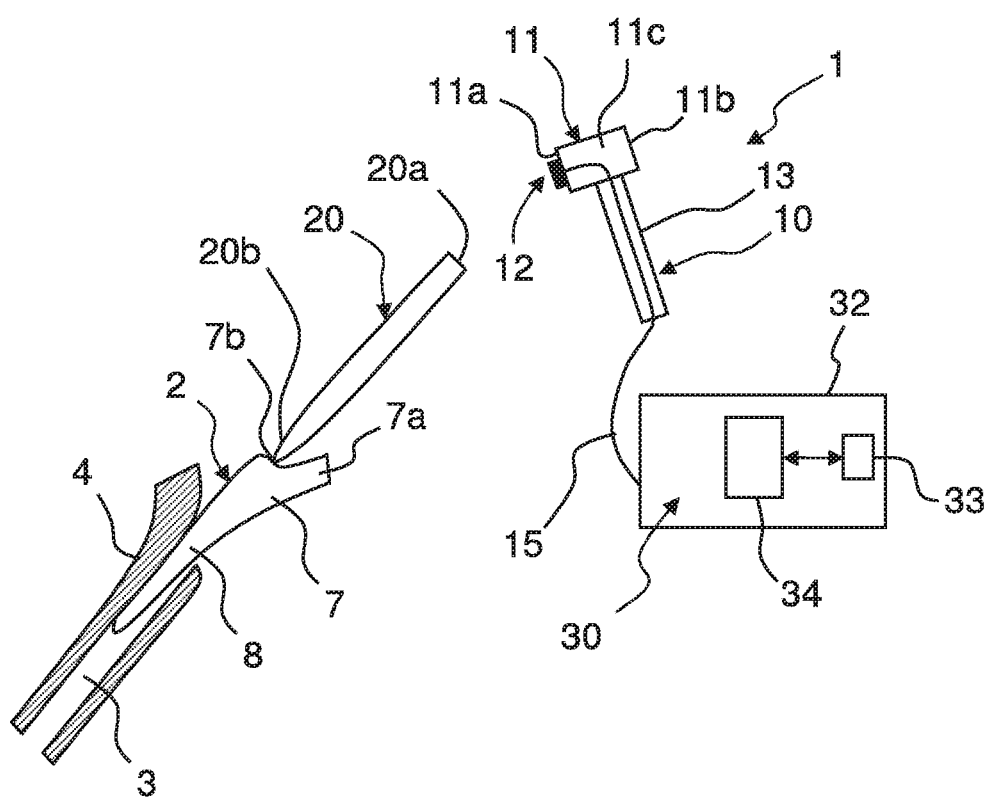
FIG. 1 schematically shows a device for inserting a surgical implant, comprising an impactor having a force sensor.

In this example, the ancillary tool 20 is a rod having a rear end forming an impact surface 20a and a front end 20b designed to come into contact with the bearing surface 7b of the stem 2. The front end 20b of the ancillary tool 20 may interact with the stem 2 by simple contact with the bearing surface 7b or be mechanically attached to the stem in a removable manner, for example by screwing. In the latter case, the front end 20b of the ancillary tool 20 may be threaded so as to be screwed into a tapped hole (not shown) formed in the contact surface 7b. The front and the rear are defined in this case with respect to the direction of forward travel of the stem 2 and the ancillary tool 20 during impaction.

The device 1 also comprises a percussion tool or impactor 10, such as a hammer or equivalent, comprising a gripping shaft 13 topped by a striking head 11. The striking head 11 has a striking face 11a for impacting the impact surface 20a of the ancillary tool 20, an opposite face 11b, opposite to the striking face 11a, and side faces 11c extending between the striking face 11a and the opposite face 11b. When the practitioner wishes to embed the femoral stem 2 in the femur 4, he grasps the ancillary tool 20 with one hand and the gripping shaft 13 of the impactor 10 with the other hand. He then strikes the impact surface 20a of the ancillary tool 20 with the striking face 11a of the impactor. The impact force generated by the impactor 10 is transmitted to the femoral stem 2 via the ancillary tool 20.

In the example of FIG. 1, the impactor 10 has a force sensor 12 for measuring the impact force exerted on the implant by the impactor 10 and providing a measurement signal representing the temporal variation of the impact force during an impact. An example of a force sensor of this type is described in patent document FR 3019031. During insertion of a femoral stem 2 as shown in FIG. 1, such a force sensor 12 is capable of converting the impact force applied to the impact surface 20a of the ancillary tool 20 upon each strike, into an exploitable electrical signal. The sensor is, for example, a gauge sensor or a piezoelectric sensor connected appropriately to the processing unit 30. In the example shown, the force sensor 12 is secured to the striking face 11a of the head 11 of the impactor 10. As an alternative, the force sensor 12 may be positioned on the impact surface 20a of the ancillary tool 20, or even at the interface between the ancillary tool 20 and the femoral stem. In applications not using an ancillary tool, the force sensor 12 may be positioned on the surface of the implant 2 which forms the impact surface.

The device also includes a processing unit 30 connected to the sensor 12 and configured to quantify the contact between the stem 2 and the receiving bone, i.e. the femur 4, on the basis of the measurement signals delivered by the sensor 12. This processing unit 30 comprises, for example, a microcontroller 34. The processing unit 30 may be housed in an external housing 32. As an alternative, the processing unit 30 may be integrated in the impactor 10. According to another alternative, the processing unit 30 may be formed of separate elements such as a microcomputer connected to a data acquisition module itself connected to the sensor 12.

The connection between the sensor 12 and the processing unit 30 is, in the example of FIG. 1, wired by means of a cable 15. As an alternative, the measurement signals supplied by the sensor 12 may be transmitted by means of a wireless connection, in which case the sensor 12 is equipped with an antenna or equivalent.

During each impact performed by the practitioner on the stem 2 by means of the impactor 10, via the ancillary tool 20, the sensor 12 measures the impact force exerted and supplies a measurement signal representing the temporal variation of this force during the impact. It is considered that the impact begins from the instant the impactor 10 and the implant come into contact, directly or indirectly (i.e. via the ancillary tool 20), and lasts for a certain period of time after this instant. Anyway, this period of time is less than 50 ms. Examples of signals supplied by the sensor 12 are shown in FIG. 2 and described below.

The inventors decided to take look at such a measurement signal and established that this signal carried information on the level of contact between the femur 4 and the stem 2. In particular, the inventors succeeded in determining, on the basis of the measurement signal collected, an indicator representative of the level of contact between the femur 4 and the stem 2, as explained below.

In an attempt to explain the link between the measurement signal collected and the level of stem-femur contact, the following explanation can be offered. The impactor 10 exerts on the stem 2, via the ancillary tool 20, an impact force which is the source of modes of vibration in the whole system made up of the impactor 10, the sensor 12, the ancillary tool 20, the femoral stem 2 and the femur 4 when these elements are all in contact during impact. These modes of vibration essentially depend on the modes of vibration of the bone-implant system (i.e. of the femur-stem system) which in turn depend on the level of contact between the implant and the bone. In essence, the greater the level of bone-implant contact, the more rigid the bone-implant system and the higher the resonance frequencies of the modes of vibration.

Figure 2:
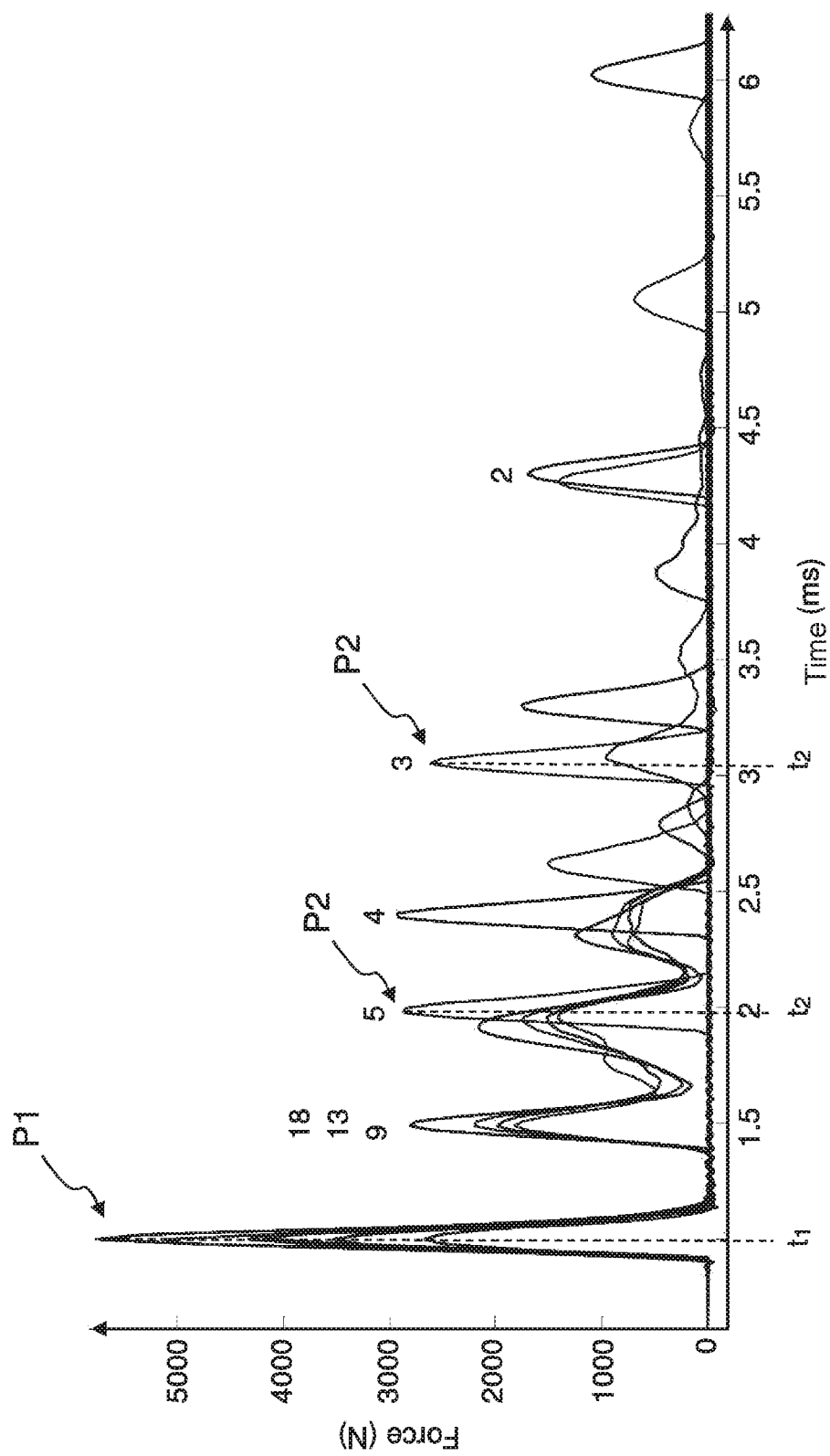
FIG. 2 schematically shows an example of signals obtained using the force sensor of FIG. 1, during the insertion of the implant.

FIG. 2 is a graph schematically showing an example of signals obtained using the force sensor 12 during a test of insertion of a femoral stem 2 into the femur 4 of a corpse. The time (t) in milliseconds (ms) is plotted on the X-axis, and the force measured by the sensor 12, in newtons (N), is plotted on the Y-axis.

Several signals are shown in FIG. 2. Each signal corresponds to an impact. In total, during this insertion test, twenty-five impacts were inflicted on the femoral stem 2. However, for the sake of better visibility, only the signals corresponding to the second, third, fourth, fifth, ninth, thirteenth, eighteenth and twenty-fourth impacts are shown in FIG. 2. For each signal, two first peaks of maximum amplitude are clearly visible.

Each impact is inflicted at time t=0. The first peak of maximum amplitude P1 appears almost instantaneously (i.e. one millisecond after), at time t1. The first peaks P1 of the various signals are superimposed in time in FIG. 2, the X-axis t1 of the first peak P1 being the same for each impact. The amplitude of the first peak P1 reflects the impact force exerted during the impact.

The second peak of maximum amplitude appears a few tenths of a millisecond to a few milliseconds after the first peak P1. As stated above, only the signals corresponding to impacts of rank 2, 3, 4, 5, 9, 13, 18 and 24 are shown in FIG. 2. These ranks are indicated above the second peaks of maximum amplitude of the corresponding signals. The second peak appears at instant t2. In FIG. 2, the second peak is identified and denoted P2 only for the third and fifth impact (or impacts of rank 3 and 5). Similarly, the instant t2 is identified only for the third and the fifth impact.

As shown in FIG. 2, the duration (t2-t1) between the first and second peaks P1, P2 decreases as a function of the rank of the impact and the inventors established that this duration (t2-t1) was a reliable indicator IN1 relevant for reflecting the level of contact between the femoral stem 2 and the femur 4.

Figure 3:
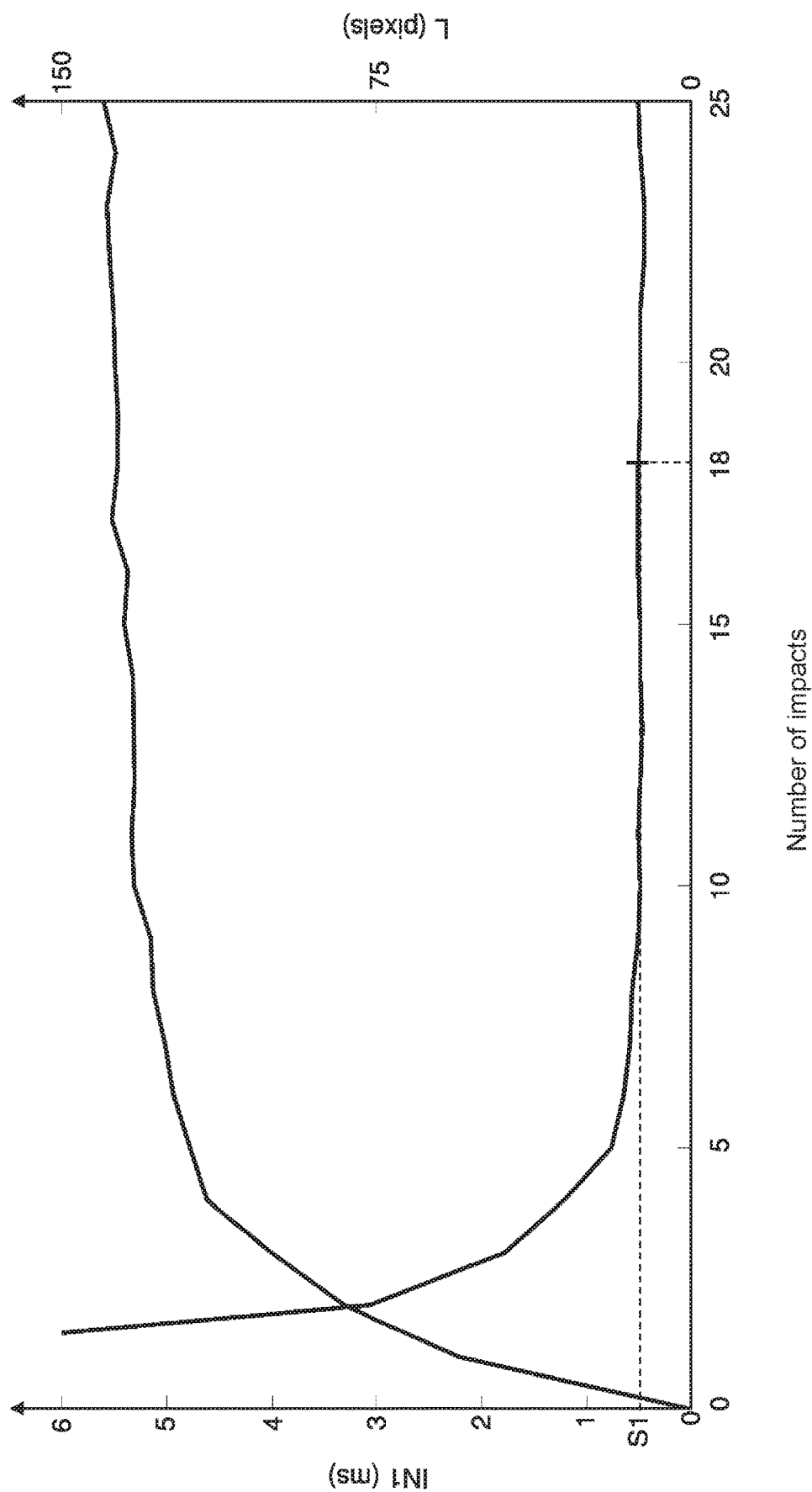
FIG. 3 schematically shows the variation in the indicator selected and the variation in the embedding of the implant as a function of the number of impacts.

FIG. 3 is a graph showing the evolution of the indicator IN1 as a function of the number of impacts and the evolution of the embedded length L of the stem 2 as a function of the number of impacts during the same insertion test as that of FIG. 2. The insertion of the stem 2 into the femur 4 was filmed and the length L was measured in the video images. The number of impacts (from 1 to 25) is plotted on the X-axis. The indicator IN1, expressed in milliseconds (ms), is plotted on the Y-axis. The length of stem L embedded in the femur 4, measured in the video images and expressed in number of pixels, is also plotted on the Y-axis.

As shown in FIG. 3, in general, the greater the embedded length L of the femoral stem 2 in the femur, and therefore the greater the surface area of the stem 2 in contact with the femur 4, the lower the indicator IN1. Initially, the embedded length L increases rapidly and the indicator IN1 decreases rapidly. Then, after a certain number of impacts, the stem is "docked" and barely sinks in any further despite the impacts. This is reflected in FIG. 3 by a plateau in the evolution of the embedded length L. At this time, the surface area of the stem 2 in contact with the femur 4 is at a maximum and barely changes despite the impacts. Note that, at the same time, the indicator IN1 also reaches a plateau. This graph illustrates the fact that the indicator IN1 is relevant for representing the level of contact between the stem 2 and the femur 4.

In addition, in this insertion test, it was considered (notably on the basis of the video images recorded) that the level of stem-femur contact was optimal, or in any case sufficient, from the $18^{th}$ impact. On this basis, the value of the indicator IN1 at the $18^{th}$ impact may be chosen as the threshold value S1 for configuring the processing unit 30. In this example, the threshold value S1 was chosen as equal to 0.32 ms. Of course, this is only an example, and other tests could be carried out, as an alternative or in combination, to determine the threshold value S1 corresponding to a level of stem-femur contact deemed sufficient. Typically, the threshold value S1 is between 0.1 and 1 ms.

Once determined, the threshold value S1 can be used to configure the insertion device 10. This threshold value S1 is, for example, recorded in the memory of the processing unit 30. Moreover, the device 10 may include an alert system 33 for emitting an alert signal (for example, an audio, visual and/or tactile signal). The alert system 33 is connected to the processing unit 30 and interacts with the latter to alert the practitioner when the level of contact between the stem 2 and the femur 4 is deemed sufficient on the basis of the indicator IN1, i.e., in this example, as soon as the indicator IN1 drops below the threshold value S1. Consequently, the practitioner has reliable information in real time indicating that he has reached a sufficient level of stem-femur contact. He concludes that he can stop impacting the stem 2, which reduces the risk of damaging the femur 4, in particular of inducing a fracture or microcracks in the femur 4.

The example which has just been described, concerning the insertion of a femoral stem into a femur, is given by way of non-limiting illustration, and a person skilled in the art could easily use the indicator proposed by the inventors with other types of implants, without departing from the scope of the invention. In other words, the stem 2 and the femur 4 are only examples of a surgical implant and a receiving bone, respectively, within the meaning of the invention.

In particular, the proposed device may be used for implants for a hip prosthesis other than a femoral stem (e.g. for acetabular implants), implants for a knee, shoulder, spine, ankle, etc. prosthesis and, more generally, any type of surgical implant requiring forcible insertion into a receiving bone by impaction. It may also be used for the insertion of surgical instruments temporarily inserted into the body of a patient and, for example, for the insertion of a surgical rasp such as a femoral rasp for a hip prosthesis. Femoral rasps are designed to be forcibly inserted, by impaction, into the medullary canal in order to prepare this canal to receive the femoral stem. These rasps are impacted directly by an impactor, with or without the intermediary of an ancillary tool. If no ancillary tool is used, the impact surface is then constituted by a surface located at the rear end of a gripping part of the rasp.

Moreover, the example which has just been described uses a force sensor 12. According to another example (not shown), it is possible to use a deformation sensor capable of providing a measurement signal representing the temporal variation of the deformation of the impactor 10 during an impact. During insertion of a femoral stem 2 as shown in FIG. 1, such a deformation sensor is capable of converting the deformation of the striking head 11 of the impactor 10 into an exploitable electrical signal. In this case, instead of being located on the striking face 11a like the force sensor 12, the deformation sensor is positioned on one of the side faces 11c of the striking head 11. In this case, the deformation sensor is positioned on the side face 11c extending parallel to the direction of the axis of the gripping shaft 13. More specifically, seen from the side (as in FIG. 1), the deformation sensor is secured to the front part of the side face 11c, between the striking face 11a and the axis of the gripping shaft 13. The front and the rear are defined in this case with respect to the striking movement of the impactor 10. The deformation sensor is secured to the striking head 11, for example by adhesive bonding or any other suitable securing means, such that the deformation of the striking head 11 causes the deformation of the sensor. The sensor is, for example, a gauge sensor comprising an elastic measurement element, the deformation of which is first converted into a variation in the electrical resistance of the gauge, to then generate an electrical output signal. Alternatively, it may be a piezoelectric sensor based on the piezoelectric properties of a material (e.g. quartz or synthetic ceramics) which generates an electrical charge when it deforms.

The measurement signal supplied by such a deformation sensor and representing the temporal variation of the deformation of the impactor during an impact also has first and second peaks of maximum amplitude. The period of time separating these two peaks also proves to be a reliable indicator relevant for evaluating the level of contact between the implant and the receiving bone.

Lastly, the various features of the embodiments or examples described in the present disclosure may be considered in isolation or be combined with one another. When they are combined, these features may be as described above or otherwise, the invention not being limited to the specific combinations described above. In particular, unless otherwise specified or technically incompatible, a feature described in relation to one embodiment or example may be applied in a similar manner to another embodiment or example.

The invention claimed is:

1. A device for forcibly inserting an implant into a receiving bone, by impaction, comprising:
   an impactor adapted for impacting an impact surface coupled to the implant and exerting an impact force on the implant,
   at least one sensor associated with the impactor, and
   a processing unit connected to the at least one sensor, wherein:
   the at least one sensor is capable of measuring a magnitude out of the impact force exerted and a deformation of the impactor, and of providing a measurement signal representing a temporal variation of said magnitude during an impact,
   the processing unit is configured to calculate, based on the temporal variation of said magnitude during the impact, an indicator representative of a level of contact between the implant and the receiving bone, and
   the indicator corresponds to a duration of a time window, a start of the time window being defined with respect to an instant corresponding to a first peak of maximum amplitude of the measurement signal and an end of the time window being defined with respect to an instant corresponding to a second peak of maximum amplitude of the measurement signal.

2. The device according to claim 1, further comprising an alert system connected to the processing unit and interacting with the processing unit so as to emit an alert signal when the indicator becomes less than a predetermined threshold value.

3. The device according to claim 2, wherein the predetermined threshold value is between 0.1 and 1 ms.

4. The device according to claim 1, wherein the processing unit is configured to detect, in the measurement signal, the first peak of maximum amplitude and an additional peak of maximum amplitude following the first peak, the additional peak being considered as the second peak of maximum amplitude only if an amplitude of the measurement signal between the first peak and the additional peak becomes less than a predetermined limit value.

5. The device according to claim 4, wherein the predetermined limit value is between 1 and 20% of the maximum amplitude of the first peak.

6. The device according to claim 1, wherein the impactor has a striking face for impacting the impact surface, an opposite face, opposite to the striking face, and side faces extending between the striking face and the opposite face, and wherein the at least one sensor comprises a deformation sensor adapted for measuring a deformation of the impactor and providing a measurement signal representing a temporal variation of the deformation of the impactor during an impact.

7. The device according to claim 1, wherein the impactor has a striking face for impacting the impact surface and wherein the at least one sensor comprises a force sensor adapted for measuring the impact force and providing a measurement signal representing a temporal variation of the impact force during an impact.

8. The device according to claim 1, wherein the impactor is a hammer, or equivalent, and comprises a gripping shaft topped by a striking head.

9. The device according to claim 1, further comprising an ancillary tool having a rear end forming said impact surface and a front end adapted for cooperating with the implant, the impactor exerting the impact force on the implant via the ancillary tool.

10. An assembly comprising a device according to claim 1 and a surgical implant.

11. The assembly according to claim 10, wherein the device comprises an ancillary tool having a rear end forming said impact surface and a front end adapted for cooperating with the implant, the impactor exerting the impact force on the implant via the ancillary tool, wherein the front end of the ancillary tool is mechanically attached to the implant in a removable manner.

12. The assembly according to claim 11, wherein the front end of the ancillary tool is attached to the implant by screwing.

13. The assembly according to claim 10, wherein the surgical implant is a femoral stem.

14. A method for forcibly inserting a surgical implant into a receiving bone, by impaction, wherein:
   a device according to claim 1 and the surgical implant are provided,
   an impact force is exerted on the implant with the impactor, by impacting an impact surface coupled to the implant, so as to insert the implant,
   the indicator is calculated during successive impacts, and impacting of the impact surface is stopped when the indicator becomes less than a predetermined threshold value.

15. The method according to claim 14, wherein the surgical implant is a femoral stem, and wherein the femoral stem is impacted with the impactor so as to insert the femoral stem into a medullary canal of a femur.

* * * * *